United States Patent [19]

Grögler et al.

[11] 4,438,250

[45] Mar. 20, 1984

[54] SUSPENSIONS OF ISOCYANATO UREAS IN ISOCYANATE PREPOLYMERS, A PROCESS FOR THEIR PRODUCTION AND THEIR USE IN THE PRODUCTION OF HIGH MOLECULAR-WEIGHT POLYURETHANE PLASTICS

[75] Inventors: Gerhard Grögler; Otto Ganster, both of Leverkusen; Klaus Recker, Cologne, all of Fed. Rep. of Germany

[73] Assignee: Bayer Aktiengesellschaft, Leverkusen, Fed. Rep. of Germany

[21] Appl. No.: 112,481

[22] Filed: Jan. 16, 1980

[30] Foreign Application Priority Data

Jan. 23, 1979 [DE] Fed. Rep. of Germany ....... 2902469

[51] Int. Cl.³ .............................................. C08G 18/38
[52] U.S. Cl. ....................... 528/66; 525/457; 528/59; 528/67; 528/84
[58] Field of Search ...................... 528/66, 59, 67, 84; 525/457

[56] References Cited

U.S. PATENT DOCUMENTS

| | | | |
|---|---|---|---|
| 2,597,025 | 5/1952 | Orth | 528/44 |
| 2,757,184 | 7/1956 | Pelley | 260/453 |
| 2,757,185 | 7/1956 | Barthel | 260/453 |
| 2,858,298 | 10/1958 | Burt | 260/77.5 |
| 2,902,474 | 9/1959 | Arnold et al. | 528/66 |
| 3,023,228 | 2/1962 | Wagner et al. | 260/471 |
| 3,906,019 | 9/1975 | Campbell et al. | 260/453 |

FOREIGN PATENT DOCUMENTS 842338 7/1960 United Kingdom .
1369334 10/1974 United Kingdom .

*Primary Examiner*—Harold D. Anderson
*Attorney, Agent, or Firm*—Gene Harsh; Joseph C. Gil; Lyndanne M. Whalen

[57] ABSTRACT

The invention is directed to suspensions of isocyanato ureas in isocyanate prepolymers; to a process for their production by reacting mixtures of aromatic diisocyanates containing isocyanate groups of different reactivities and prepolymers containing terminal isocyanate groups, with water; and to the use of the suspensions as synthesis components in the production of polyurethane plastics.

3 Claims, No Drawings

SUSPENSIONS OF ISOCYANATO UREAS IN ISOCYANATE PREPOLYMERS, A PROCESS FOR THEIR PRODUCTION AND THEIR USE IN THE PRODUCTION OF HIGH MOLECULAR-WEIGHT POLYURETHANE PLASTICS

BACKGROUND OF THE INVENTION

This invention relates to suspensions of isocyanato ureas in isocyanate prepolymers; to a process for their production by reacting mixtures of aromatic diisocyanates containing isocyanate groups of different reactivities and prepolymers containing terminal isocyanate groups, with water; and to the use of the suspensions as synthesis components in the production of polyurethane plastics.

It has long been known that the reaction of water with monoisocyanates gives substituted ureas and, with polyisocyanates, gives polyureas of high molecular weight. According to U.S. Pat. No. 2,597,025, resin-like polyureas containing isocyanate groups can be obtained by using from 0.3 mol of $H_2O$ per mol of aromatic diisocyanate in suitable solvents. In addition, it is known that aromatic diisocyanates can also be selectively reacted with water to form low molecular weight diisocyanato ureas. Thus, according to U.S. Pat. Nos. 2,757,184, 2,757,185 and 3,906,019, the reaction of 2,4-diisocyanatotuluene with water under suitable conditions gives the corresponding bis-(3-isocyanatotolyl)-urea.

The analogous reaction of 2,6-diisocyanatotoluene to form the corresponding 1,3-bis-(3-isocyanatotolyl)-urea is also known (U.S. Pat. Nos. 3,906,019 and 2,902,474).

All of these processes are carried out in solvents. The isocyanates must be highly soluble. The water added must be at least partly soluble in the solvents used. The solvent must not have any polymerizing effect on the isocyanate and must be free from isocyanate-reactive functional groups. The isocyanate ureas are precipitated in the form of substantially insoluble compounds and are isolated by filtration. For further processing for polyurethane reactions, these isocyanate ureas obtained by filtration and freed from the solvents in vacuo must be converted into a finely divided form by grinding operations. Due to the high melting point and to the poor solubility of these isocyanate ureas, inhomogeneous products are obtained in many cases during the further reaction.

Isocyanato ureas, particularly bis-isocyanato ureas of low molecular weight, are particularly valuable starting materials for the production of polyurethane plastics because the urea groups incorporated during their use provide the plastics with very good mechanical properties.

Accordingly, the object of the present invention is to provide bis-isocyanato ureas by a simple process and in a form which enables them to be further processed without difficulty into high molecular weight polyurethanes.

DESCRIPTION OF THE INVENTION

According to the present invention, this object surprisingly is achieved by mixing aromatic diisocyanates containing isocyanate groups of different reactivities with prepolymers containing terminal isocyanate groups and selectively reacting the resulting mixture with water to form the bis-isocyanato urea which then accumulates in the form of a readily processible suspension in the prepolymer. It is surprising that such a selective reaction is possible because the isocyanate groups of prepolymers are known to react completely with water, even at low temperatures, to form high molecular weight plastics with the evolution of carbon dioxide. Accordingly, it had been expected that the aromatic diisocyanates would be unable to be selectively converted into the corresponding bis-isocyanato ureas in the presence of the prepolymers containing NCO-groups. Surprisingly, however, the prepolymer undergoes hardly any chain extension during the process of the invention.

The present invention is directed to suspensions which are liquid at room temperature or which can be liquefied by heating to at most 80° C. (including materials paste-like at room temperature but liquefiable by heating to no more than 80° C.) of (a) isocyanato ureas corresponding to the following general formula:

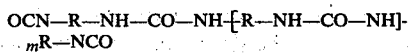

wherein
R represents a difunctional aromatic radical of the type obtained by removing the isocyanate groups from an aromatic diisocyanate, and
m represents 0 or an integer from 1 to 5, in (b) isocyanate prepolymers corresponding to the following general formula:

wherein
A represents a radical of the type obtained by removing the isocyanate groups from an organic diisocyanate,
D represents a radical of the type obtained by removing the hydroxyl groups from an n-functional polyhydroxyl compound having a molecular weight in the range of from 500 to 8,000, and
n represents an integer from 2 to 4.

The present invention also relates to a process for producing the above suspensions characterized in that aromatic diisocyanates corresponding to the following general formula:

R(NCO)₂ wherein R is defined as above, are mixed with isocyanate prepolymers corresponding to the following general formula:

D+O—CO—NH—A—NCO)ₙ wherein A, D, and n are defined as above, and the resulting mixture is reacted with from 0.4 to 0.8 mol of water per mol of the aromatic diisocyanate or with a corresponding quantity of a dehydrating agent.

Additionally, the invention is directed to the use of the suspensions as the isocyanate component in the isocyanate polyaddition process for the production of polyurethane plastics.

In one preferred embodiment of the invention the variables appearing in the above-mentioned formulas are as follows:

A represents a radical of the type obtained by removing the isocyanate groups from an organic diisocyanate and is an optionally alkyl-substituted aromatic hydrocarbon radical containing a total of from 6 to 15 carbon atoms, an aliphatic hydrocarbon radical containing from 4 to 10 carbon atoms, a cycloaliphatic hydrocarbon radical containing from 4 to 15 carbon atoms or an araliphatic hydrocarbon radical containing 8 carbon atoms such as the xylylene radical, D represents a radical containing ester or ether groups of the type obtained by removing the hydroxyl groups from a polyester or polyether diol having a molecular weight in the range of from 500 to 8000, more particularly in the range of from 1000 to 3000, R represents a difunctional aromatic hydrocarbon radical of the type obtained by removing the isocyanate groups from an aromatic diisocyanate having a molecular weight in the range of from 174 to 400 and containing isocyanate groups of different reactivities, more particularly a 2,4-tolyl radical, m represents 0 or an integer of from 1 to 3 and n represents 2.

In the context of the present invention, aromatic diisocyanates defined as containing isocyanate groups of different reactivities are not only the above diisocyanates corresponding to the strict meaning of this definition, but also mixtures of these diisocyanates with up to 50% by weight, based on the mixture as a whole, of aromatic diisocyanates containing isocyanate groups of the same reactivity.

Diisocyanates $R(NCO)_2$, suitable for the invention include, for example, diisocyanates which, in addition to a free (i.e. sterically unhindered) aromatically bound isocyanate group, contain another aromatically bound isocyanate group which is sterically hindered by at least one substituent in the o-position to it on the aromatic ring. Particular substituents which can sterically hinder the isocyanate group when ortho to it are $C_1$–$C_8$-alkyl, $C_6$–$C_{10}$-aryl, $C_1$–$C_8$-alkoxy, $C_1$–$C_8$-alkoxyl carbonyl, chlorine, bromine or cyano groups. The aromatically bound isocyanate group also is sterically hindered when the basic skeleton of the diisocyanate is a system of several aromatic rings optionally attached through bridge members, such as alkylene, ether, sulphoxide or sulphone groups, and the (sterically hindered) isocyanate group is situated in the ortho position to the bridge member attaching two aromatic rings.

Particularly preferred aromatic diisocyanates are, for example, aromatic diisocyanates corresponding to the following general formulas:

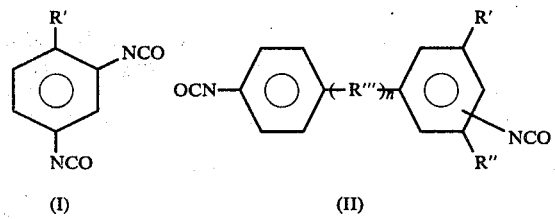

(I)                    (II)

wherein

R' and R" which may be the same or different, represent groups of the type mentioned by way of example above sterically hindering the isocyanate group, one of R' or R" in formula II may represent hydrogen (and the other a group of the type mentioned above sterically hindering the isocyanate group; both R' and R" in formula (II) may represent hydrogens) if the isocyanate group is in the ortho position to a bridge R''' or, where n=0, is in the ortho position to the left-hand aromatic radical;

R''' represents a bridge attaching the aromatic rings, of the type mentioned by way of example above, and n represents 0 or 1.

It is possible in the invention to use mixtures of aromatic diisocyanates containing aromatic diisocyanates having isocyanate groups of different reactivities and aromatic diisocyanates having isocyanate groups of the same reactivity, such as 4,4'-diisocyanatodiphenyl methane or 2,6-diisocyanatotoluene, providing the proportion of diisocyanates containing isocyanate groups of the same reactivity does not exceed 50% preferably 40% by weight of the total weight of the mixture.

Particularly preferred diisocyanates include, for example, 2,4-diisocyanatotoluene, optionally in admixture with up to 50% by weight of 2,6-diisocyanatotoluene; and 2,4'-diisocyanatodiphenyl methane, optionally in admixture with up to 50% by weight, of 4,4'-diisocyanatodiphenyl methane. Other suitable diisocyanates are, for example, 2,4'-diisocyanatodiphenyl propane, 2,4'-diisocyanato-diphenyl ether, 2,4'-diisocyanatodiphenyl sulphone, 2,4'-diisocyanatodiphenyl sulphodioxide, 3-methyl-4,4'-diisocyanatodiphenyl methane, 3-ethyl-4,4'-diisocyanatodiphenyl methane, 3-isopropyl-4,4'-diisocyanatodiphenyl methane, 3,5-dimethyl-4,4'-diisocyanatodiphenyl methane, 3,5-diethyl-4,4'-diisocyanatodiphenyl methane, 3,5-diisopropyl-4,4'-diisocyanatodiphenyl methane, 3-carboxymethyl-4,4'-diisocyanatodiphenyl methane, and 3-carboxymethyl-4,4'-diisocyanatodiphenyl methane.

Polyols of the formula:

$D(OH)_n$ suitable for producing the isocyanate prepolymers include polyesters, polyethers, polythioethers, polyacetals, polycarbonates or polyester amides containing from 2 to 4, preferably 2, hydroxyl groups and having a molecular weight in the range from 500 to 8000, preferably in the range from 1000 to 3000, of the type generally known for the production of homogeneous or foamed polyurethanes. It is preferred to use the corresponding polyester or polyether polyols.

Polyesters containing hydroxyl groups which are suitable for the invention include, for example, reaction products of polyhydric, preferably dihydric and, optionally, even trihydric alcohols with polybasic, preferably dibasic, carboxylic acids. Instead of using the free polycarboxylic acids, it is also possible to use the corresponding polycarboxylic acid anhydrides, corresponding polycarboxylic acid esters of lower alcohols, or mixtures thereof, for producing the polyesters. The polycarboxylic acids may be aliphatic, cycloaliphatic, aromatic and/or heterocyclic. They may be substituted (for example by halogen atoms) and/or they may be unsaturated. Examples of suitable polycarboxylic acids include succinic acid, adipic acid, suberic acid, azelaic acid, sebacic acid, phthalic acid, isophthalic acid, trimellitic acid, phthalic acid anhydride, tetrahydrophthalic acid anhydride, hexahydrophthalic acid anhydride, endomethylene tetrahydrophthalic acid anhydride, glutaric acid anhydride, maleic acid, maleic acid anhydride, and fumaric acid. Suitable polycarboxylic acids also include dimeric and trimeric fatty acids such as trimeric oleic acid, optionally in admixture with monomeric fatty acids. Suitable polyhydric alcohols include, for example, ethylene glycol; 1,2- and 1,3-propylene glycol; 1,4- and 2,3-butylene glycol; 1,6-hexane diol; 1,8-octane diol; neopentyl glycol; cyclohexane dimethanol (1,4-bis-hydroxymethyl-cyclohexane); 2-methyl-1,3-propane diol; glycerol; trimethylol propane; 1,2,6-hexane triol; 1,2,4-butane triol; trimethylol ethane; diethylene glycol; triethylene glycol; tetraethylene glycol; polyethylene glycols; dipropylene glycol; polypropylene glycols; dibutylene glycol and polybutylene glycols. Polyesters of lactones such as ε-caprolactone, or hydroxy carboxylic acids such as ω-hydroxy caproic acid, may also be used.

The polyethers containing from 2 to 4, preferably 2, hydroxyl groups which may be used in the invention are generally known. Such polyethers are obtained, for example, by polymerizing epoxides, such as ethylene oxide, propylene oxide, butylene oxide, tetrahydrofuran, styrene oxide or epichlorohydrin, on their own or for example in the presence of $BF_3$. Additionally such polyethers can be obtained, for example, by adding the above epoxides, optionally in admixture or successively, with starter components containing reactive hydrogen atoms, such as water, alcohols or amines. Starter components containing reactive hydrogen atoms include, for example, water, ethylene glycol; 1,3- or 1,2-propylene glycol; trimethylol propane; 4,4'-dihydroxy diphenyl propane; aniline; ammonia; ethanolamine or ethylene diamine. In many cases, it is preferred to use polyethers containing major amounts of primary OH-groups (i.e., up to 90% by weight, of all the OH-groups present in the polyether). Polyethers modified by vinyl polymers, of the type obtained for example by polymerizing styrene and acrylonitrile in the presence of polyethers (U.S. Pat. Nos. 3,383,351, 3,304,273, 3,523,093, and 3,110,695; German Patent 1,152,536) also may be used.

Particularly suitable polythioethers include the condensation products of thiodiglycol itself and/or of thiodiglycol with other glycols, dicarboxylic acids, formaldehyde, aminocarboxylic acids or amino alcohols. Depending on the co-components, the products in question are polythio mixed ethers, polythio ether esters or polythio ether ester amides.

Suitable polyacetals include, for example, the compounds obtainable from glycols, such as diethylene glycol, triethylene glycol, 4,4'-dioxethoxy diphenyl dimethyl methane, hexane diol and formaldehyde. Polyacetals suitable for use in accordance with the present invention may be obtained by polymerizing cyclic acetals.

Suitable polycarbonates containing hydroxyl groups include those generally known which may be obtained, for example, by reacting diols; such as 1,3-propane diol, 1,4-butane diol and/or 1,6-hexane diol, diethylene glycol, triethylene glycol or tetraethylene glycol; with diaryl carbonates such as diphenyl carbonate; or with phosgene.

Polyhydroxyl compounds already containing urethane or urea groups and optionally modified natural polyols, such as castor oil, may also be used.

Representatives of many of the compounds which may be used in accordance with the present invention are described, for example, in High Polymers, Vol. XVI, "Polyurethanes, Chemistry and Technology" by Saunders-Frisch, Interscience Publishers, New York, London, Vol. I, 1962, pages 32 to 42 and 44 to 54 and Vol. II, 1964, pages 5-6 and 198-199, and in Kunststoff-Handbuch, Vol. VII, Vieweg-Hochtlen, Carl-Hanser-Verlag, Munich, 1966, pages 45 to 71.

Mixtures of the above-mentioned compounds, such as mixtures of polyethers and polyesters, may be used.

Diisocyanates of the formula:

$A(NCO)_2$ suitable for producing the isocyanate prepolymers include, for example: tetramethylene diisocyanate; hexamethylene diisocyanate; 1,12-dodecane diisocyanate; cyclobutane-1,3-diisocyanate; cyclohexane-1,3- and 1,4-diisocyanate and mixtures of these isomers; 1-isocyanato-b 3,3,5-trimethyl-5-isocyanatomethyl cyclohexane; 2,4- and 2,6-hexahydrotolylene diisocyanate and mixtures of these isomers; hexahydro-1,3- and/or -1,4-phenylene diisocyanate; perhydro-2,4'- and/or -4,4'-diphenyl methane diisocyanate; 1,3- and 1,4-phenylene diisocyanate; 2,4- and 2,6-tolylenediisocyanate and mixtures of these isomers; diphenyl methane-2,4'- and/or -4,4'-diisocyanate; naphthylene-1,5-diisocyanate. Suitable diisocyanates for preparing the prepolymers also include polyisocyanates containing carbodiimide groups of the type described in German Patent 1,092,007; and diisocyanates of the type described in U.S. Pat. No. 3,492,330. It is also possible to use mixtures of these diisocyanates.

In general, it is particularly preferred to use commercially obtainable diisocyanates, for example 2,4- and 2,6-tolylene diisocyanate, and mixtures of these isomers ("TDI"), 2,4'- and/or 4,4'-diphenyl methane diisocyanate.

The isocyanate prepolymers corresponding to the following general formula:

$$D\text{-}(O\text{---}CO\text{---}NH\text{---}A\text{---}NCO)_n$$

which are used as starting materials in the invention are produced by a known method from the polyhydroxyl compounds $D(OH)_n$ and diisocyanates $A(NCO)_2$. To prepare the isocyanate prepolymers, excess quantities of the diisocyanates generally are reacted with the polyols, after which the excess unreacted diisocyanate is often removed by distillation. The molar ratios between the reactants are selected in such a way that a chain-extending reaction occurs to only a limited extent, if at all. In other words, the reaction is preferably carried out with a molar NCO/OH-ratio of at least 2:1.

The prepolymers used in the invention are either liquid at room temperature or may be liquefied simply by heating to at most 80° C.

To carry out the process the aromatic diisocyanate:

$R(NCO)_2$ is mixed with the prepolymer corresponding to the following general formula:

$$D\text{-}(O\text{---}CO\text{---}NH\text{---}A\text{---}NCO)_n.$$

The aromatic diisocyanate is added until the mixture as a whole contains from 5 to 40% by weight, preferably from 5 to 25% by weight of the diisocyanate. Then 0.4 to 0.8 mol, preferably 0.5 to 0.8 mol of water per mol of aromatic diisocyanate $R(NCO)_2$ or a corresponding quantity of a compound splitting off water is added to the above mixture. Instead of water, it is possible to use such compounds such as formic acid, tertiary alcohols such as tert.-butanol, or organic or inorganic compounds containing water of crystallization such as pinacol hexahydrate, chloral hydrate or sodium sulphate decahydrate.

The reaction generally is carried out at 20° to 80° C., preferably at 40° to 60° C.

The urea diisocyanates corresponding to the general formula:

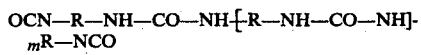

wherein m corresponds to a value within the above-mentioned range depending on the molar ratio of isocyanate to water selected, are obtained in the form of suspensions which are liquid or paste-like at room temperature or which can be liquefied by heating to at most 80° C., depending on the viscosity of the starting materials and on the concentration in which the urea diisocyanate is formed. In the case of NCO-prepolymers of relatively high polarity thus having better solvating ability for the polyisocyanate urea formed in situ, a dispersed phase occasionally is formed only after prolonged standing or by seeding. In one particular procedure, low molecular weight diisocyanates containing NCO-groups of different reactivity are directly used for preparing the relatively high molecular weight NCO-preadduct. In the production of these NCO-preadducts, the NCO/OH-ratio is adjusted in such a way that a corresponding excess of free aromatic diisocyanate is still present on completion of the polyol/isocyanate reaction.

In general, the reaction of the water with the excess aromatic diisocyanate is so complete that the suspensions formed contain only small residues of free diisocyanate. This is of physiological significance, particularly where diisocyanates of relatively high vapor pressure such as diisocyanatotoluene are used. Low-monomer suspensions having a free isocyanate content of less than 0.6% by weight are obtained particularly where a molar ratio of $H_2O$ to NCO (based on aromatic diisocyanate) of from 1:4 to 1:2.6 is used. Surprisingly, the relatively high molecular weight NCO-preadducts are not significantly crosslinked by water in this case.

It is also possible to use NCO-prepolymers melting at a temperature above 80° C. In this case in order to prevent secondary reactions such as biuret formation it is particularly advisable to use dehydrating agents, such as pinacol hexahydrate, instead of water and to add deactivating acid compounds, such as phosphoric acid, toluene sulphonic acid or benzyl chloride, in a quantity of from 0.01 to 0.1% by weight of the reaction mixture. Even where tertiary butanol is used as the dehydrating agent, these compounds are necessary for reducing the cleavage temperature of the tert.-butyl urethane initially formed.

Known compounds which accelerate the diisocyanate addition reaction, such as tertiary amines or organometallic compounds, generally are not used in the present invention in order to prevent the formation of high molecular weight polyureas free from isocyanate groups.

The course of the reaction readily may be followed and controlled by determining the volume of carbon dioxide evolved. After the solubility limit has been exceeded, the diisocyanato ureas are precipitated in a finely divided form, and largely non-sedimenting suspensions are obtained. The total NCO-content of these suspensions which generally amounts to between 5 and 15% by weight, preferably to between 5 and 10% by weight is made up of the NCO-content of the relatively high molecular weight prepolymer and the NCO-content of the suspended diisocyanate urea.

Where the suspensions of the invention are used as synthesis components in the production of polyurethane plastics, the different isocyanate groups present may be selectively reacted depending on the working conditions. Thus, where crosslinking is carried out with glycols, amines or water, a highly viscous or solid polyurethane matrix initially is rapidly formed due to crosslinking of the homogeneous NCO-prepolymer. In many cases, the reaction of the polyisocyanate urea present in the heterogeneous phase with the chain extender then takes place with some delay. The time sequence of these two crosslinking steps may be controlled due to varying degrees of substantial insolubility of the polyisocyanate ureas and due to the melting point of the polyisocyanate ureas, due to the polarity or dissolving ability of the NCO-adduct and also due to the crosslinking temperature. If desired, the second reaction step also may be carried out at a later stage. The final crosslinking of the system still not having reacted to completion, may then be carried out anytime along with shaping or forming, optionally at elevated temperature.

Another advantage of the suspensions of the invention is that even where crosslinking is carried out with a diol or a triol, moldings are obtained which already contain a corresponding proportion of stable urea groups which are known to contribute to improving the mechanical properties and thermal stability of the polyurethane systems. The delayed second reaction step favorably affects the reactivity and hence the pot life of the mixtures, because the NCO-content is not completely reacted all at once with the polyol (or diamine). In addition, the suspensions of the invention based on aromatic diisocyanates of relatively high vapor pressure, such as diisocyanatotoluene should be physiologically acceptable by virtue of their low monomer content.

Finally, depending on the quantity of polyisocyanate urea in the suspension, different hardnesses are obtained after crosslinking with glycols, water or amines.

In addition to water, suitable chain-extending agents for crosslinking the polyisocyanato urea suspensions of the invention include, in particular, glycols having a molecular weight in the range from 62 to 500. Examples of such suitable glycols are ethylene glycol; 1,2- and 1,3-propylene glycol; 1,4- and 2,3-butane diol; 1,5-pentane diol, 1,6-hexane diol; 1,8-octane diol; neopentyl glycol; 1,4-bis-hydroxy methyl cyclohexane; 2-methyl-1,3-propane diol; butene diol; butyne diol; monochorohydrin, glycerol or monoaryl ether; xylylene glycols the Diels-Alder addition product of butene diol with anthracene; quinitol, hexahydropyrocatechol; 4,4'-dihydroxy diphenol propane; dihydroxymethyl hydroquinone; hydroquinone-bis-hydroxyethyl ether; diethylene glycol; triethylene glycol; and tetraethylene glycol. Suitable glycols also include higher polyethylene glycols having a molecular weight of up to 500; dipropylene glycol; higher polypropylene glycols having a molecular weight of up to 500 and N-methyl diethanolamine. 1,4- and 2,3-butane diol; cyclic glycols such as hexahydropyrocatechol and hydroquinone-bis-hydroxyethyl ether; and thiodiglycol are particularly suitable.

Where water is used as the chain-extending agent, foamed cellular moldings are obtained. In order to prevent the formation of a foam, the foamed product may be compression-molded in known manner.

Examples of aromatic diamines suitable for crosslinking are bis-anthranilic acid esters of the type described in German Offenlegungsschriften Nos. 2,040,644 and 2,160,590; 3,5- and 2,4-diaminobenzoic acid esters of the type described in German Offenlegungsschrift No. 2,026,900; the diamines containing ester groups described in German Offenlegungsschriften Nos. 1,803,635, 2,040,650 and 2,160,589; 3,3'-dichloro-4,4'-diaminodiphenyl methane; 3,3'-dithioether-4,4'-diamino-diphenyl methane; phenylene diamines; tolylene diamines; 3,5-diethyl-2,4-diaminotoluene; 4,4'-diaminodiphenyl methane and 4,4'- or 2,2'-diaminodiphenyl disulphide.

Plasticizers, dyes and fillers generally known optionally may be added at any stage of the process or at any stage in the use of the suspensions. Suitable plasticizers include, for example, phthalic acid esters and organic sulphonamides. In many cases, it is particularly favorable to use sulphur-containing plasticizers such as methylene-bis-thioglycolic acid butyl ester. As with natural rubber, some fillers improve the mechanical properties of the polyurethane elastomers produced by the invention. Such fillers include, for example, titanium dioxide, silicon dioxide, bentonite, calcium silicate and carbon black. These fillers may be directly added to the relatively high molecular weight polyhydroxyl compound or may even be incorporated into the NCO-prepolymer.

The polyurethane elastomers produced using the invention have an excellent range of mechanical properties and show high resistance to organic solvents and oils. These properties enable the elastomers to be used for a wide variety of purposes, including for example, coverings for rollers, elastic components for machines, seals, pads, syphons, linings for ball mills, shoe soles, gear-wheels and vehicle tires.

The invention is illustrated by the following Examples in which the quantities quoted represent parts by weight or percentages by weight, unless otherwise indicated.

EXAMPLES

EXAMPLE 1

174 g (1.0 mol) of 2,4-diisocyanatotoluene are added to and mixed with 2348 g (1 mol) of an NCO-prepolymer having an NCO-content of 3.5% produced from 2000 g of a linear polypropylene glycol ether having a molecular weight of 2000 (OH-number 56) and 348 g (2.0 mols) of 2,4-diisocyanatotoluene. 9 g (0.5 mol) of water are added to this mixture over a period of 30 minutes at a temperature of from 50° to 60° C. after which the mixture is kept at that temperature for 5 to 6 hours. After the evolution of $CO_2$ has stopped (11 liters), a polyisocyanate urea suspension having a total NCO-content of 4.9% and a viscosity of 10,500 mPa.s/25° C. is obtained.

EXAMPLE 1b

If 348 g (2.0 mols) of 2,4-diisocyanatotoluene are added to the above NCO-prepolymer and the mixture reacted with 18 g (1.0 mol) of water at 60° C., a polyisocyanate urea suspension having a total NCO-content of 6.0% and a viscosity of 18,000 mPa.s/25° C. is obtained after 8 to 10 hours. 23 liters of $CO_2$ are given off. The polyisocyanate urea isolated from this suspension by precipitation with ether has an NCO-content of 16.5%.

EXAMPLE 2

9 g (0.5 mol) of water are added to mixtures of 1000 g of the NCO-prepolymer mentioned in Example 1 (NCO-content 3.5%) and each of (a) 174 g (1.0 mol) of 2,4-diisocyanatotoluene
(b) 174 g (1.0 mol) of diisocyanatotoluene (2,4- and 2,6-isomer in a ratio of 80:20),
(c) 174 g (1.0 mol) of diisocyanatotoluene (2,4- and 2,6-isomer in a ratio of 65:35).

The three reaction mixtures are kept at from 50° to 60° C. until the evolution of $CO_2$ is over. Thereafter all three polyisocyanate urea suspensions have a total NCO-content of from 6.1 to 6.2% (calculated 6.2%). The following viscosity levels clearly show, however, that the selective reaction of water is seriously affected by increasing amounts of 2,6-diisocyanatotoluene. Viscosities of the polyisocyanate urea suspensions:

(a) 15,000 mPa.s/25° C.
(b) 18,000 mPa.s/25° C.
(c) 80,000 mPa.s/25° C.

EXAMPLE 3

An NCO-prepolymer having excess aromatic diisocyanate is produced by a known method from 2000 g of a linear polypropylene glycol ether having a molecular weight of 2000 (OH-number 56) and 522 g (3.0 mols) of 2,4-diisocyanatotoluene. The NCO-content amounts to 6.6% (calculated 6.7%). Increasing quantities of water are added to 2000 g of this NCO-prepolymer at 50° to 60° C. and, after the evolution of $CO_2$ has stopped (about 6 hours), the NCO-content and the free 2,4-diisocyanatotoluene content are measured. As can be seen from the following Table, the polyisocyanato ureas are precipitated after approximately 80% of the quantity of water calculated for the free low molecular weight diisocyanate (7.0 g) has been added, and polyisocyanate urea suspensions containing only very small amounts of monomer are obtained with increasing additions of water.

| Water (g) | $CO_2$(l) | NCO (total) | Free di-isocyanate | Phase |
|---|---|---|---|---|
| 4.3 | 5.0 | 4.6 | 2.0 | homogeneous |
| 5.0 | 5.3 | 4.0 | 1.5 | homogeneous |
| 5.7 | 5.8 | 4.0 | 0.75 | ↓ |
| 6.2 |  | 3.95 | 0.55 | increasingly |
| 6.7 | 6.8 | 3.9 | 0.5 | dispersed |
| 7.0 | 7.4 | 3.8 | 0.4 | phase |

EXAMPLE 4

9.5 g of pinacol hexahydrate are added all at once to an NCO-prepolymer having an NCO-content of 9.8% produced from 1000 g of a linear polypropylene glycol ether having a molecular weight of 2000 (OH-number 56) and 258 g of 2,4-diisocyanatotoluene (corresponding to 0.54 mol of $H_2O$ per mol of free TDI). A polyisocyanate urea suspension having a total NCO-content of 5.5% and a viscosity of 14,500 mPa.s/25° C. is obtained after 5 to 6 hours at from 60° to 70° C. 11 liters of carbon dioxide were given off.

EXAMPLE 5

2,4-diisocyanatotoluene and water are added in the quantities indicated in the following Table to an NCO-prepolymer having an NCO-content of 3.5% produced from 1000 g of a linear polypropylene glycol ether having a molecular weight of 2000 and 168 g of 1,6-diisocyanatohexane. Polyisocyanate urea suspensions having the properties indicated are obtained.

|  | A | B | C |
|---|---|---|---|
| 2,4-diisocyanato-toluene | 348 g (2.0 mols) | 261 g (1.5 mols) | 174 g (1.0 mols) |
| Water | 18 g (1.0 mol) | 13.5 g (0.75 mol) | 9 g (0.5 mol) |
| Temperature | 60° | 60° | 60° |
| CO$_2$-quantity (1) | 20 | 16 | 11 |
| Total NCO (%) | 8.7 | 7.5 | 6.5 |
| NCO content of the isolated polyisocyanate urea (%) | 19.5 | 13.5 | 11.8 |
| Viscosity (mPa.s/20° C.) | paste, spreadable | approx. 45,000 | 10,000 |

EXAMPLE 6

1000 g of th NCO-prepolymer mentioned in Example 5 are mixed with 126 g (0.5 mol) of 2,4'-diisocyanatodiphenyl ether, followed by the addition of 4.5 g of water. After 3 hours at 60° C., 5.5 liters of CO$_2$ have been given off and a polyisocyanate urea suspension having an NCO-content of 5.3% is obtained.

EXAMPLE 7

18.0 g (1.0 mol) of water are added dropwise over a period of 30 minutes at 60° C. to an NCO-prepolymer (NCO-content 9.4%) produced from 2000 g of a linear polyester of adipic acid and ethylene glycol (molecular weight 2000, OH-number 56) and 696 g (4.0 mols) of 2,4-diisocyanatotoluene. After about 5 hours, 19 liters of CO$_2$ have been given off and the polyisocyanate urea suspension has an NCO-content of 6.1%.

EXAMPLE 8

In a series of tests, different quantities of 2,4-diisocyanatotoluene were additionally added to an NCO-prepolymer (NCO-content 3.8%) of the polyester mentioned in Example 7 and 2,4-diisocyanatotoluene. The following reaction with water gives the polyisocyanate urea suspensions specified in the following Table to which an aromatic diamine was added in a second reaction step (Example 12).

|  | A | B | C | D |
|---|---|---|---|---|
| NCO-prepolymer NCO = 3.8% (G) | 950 | 900 | 850 | 800 |
| 2,4-diisocyanato-toluene (g) | 50 | 100 | 150 | 200 |
| Water (g) | 2.8 | 5.6 | 8.4 | 11.2 |
| Polyisocyanate urea suspension (NCO-content) | 4.9 | 6.0 | 7.1 | 8.15 |

EXAMPLE 9

1000 g of the NCO-prepolymer mentioned in Example 5 are stirred with 374 g of a mixture of 60% of 2,4'- and 40% of 4,4'-diisocyanatodiphenyl methane. 13.5 g of water are added dropwise over a period of 0.75 hours at 60° C., after which the reaction mixture is kept at this temperature for 4 hours. After 18 liters of CO$_2$ have been given off, the polyisocyanate urea suspension is obtained in the form of a spreadable paste. It has an NCO-content of 6.8%.

EXAMPLE 10

870 g (0.5 mols) of 2,4-diisocyanatotoluene are mixed with 3000 g of a branched polypropylene glycol ether having a molecular weight of 3000 (starter molecule: trimethylol propane, OH-number: 56) and the resulting mixture heated at 80° C. until it has an NCO-content of 7.5%. 18 g of water are then added dropwise over a period of 30 minutes at 60° C. After about 6 hours, 20 liters of CO$_2$ have been given off and a polyisocyanate urea suspension having an NCO-content of 4.8% and a viscosity of 15,000 mPa.s/25° C. is obtained.

EXAMPLE 11

100 parts by weight of the polyisocyanate urea suspension produced in accordance with Example 1b (NCO-content 6.0%) are degassed in vacuo at from 60° to 80° C. and stirred for 30 seconds with 17.3 g of 3,5-diethyl-2,4-diaminotoluene. One half of the reaction mixture is poured into a metal mold heated to 60° C. and the other half into a metal mold heated to 120° C. The pouring time amounts to approximately 2 minutes. After about 10 minutes, the molding can be removed. After tempering the one half of the mixture for 24 hours at 60° C. and the other half for 24 hours at 120° C., the mechanical properties of the elastomers are then determined and are as follows:

|  | Part Tempered at 60° C. | Part Tempered at 120° C. |
|---|---|---|
| Tensile strength (DIN 53504) in mPa | 8.5 | 19.5 |
| % Elongation at break (DIN 53504) | 380 | 550% |
| Tear propagation resistance (DIN 53515) in KN/m | 20.0 | 33 |
| Shore hardness A (DIN 53505) | 79 | 83 |
| Elasticity (DIN 53512) in % | 55 | 56 |

The increase in tensile strength, elongation at break and tear propagation resistance for similar hardness shows that the second reaction step, i.e. the reaction of the polyisocyanate urea with the aromatic diamine, was complete only after tempering at 120° C.

EXAMPLE 12

Quantities of 100 parts by weight of the polyisocyanate urea suspensions produced in accordance with Example 8 are degassed in vacuo at from 80° to 100° C. and subsequently stirred for 30 seconds with the indicated amount of 2,5-diamino-4-chlorobenzoic acid isobutyl ester. In every case, the NCO/NH$_2$ equivalent ratio amounts to 1.1:1. The reaction mixtures are poured into waxed molds heated to 100° C. The pouring time amounts to between 2 and 5 minutes. Moldings having the properties indicated below are obtained after tempering for about 10 hours at 120° to 130° C. The NCO content of the NCO-prepolymer used in each case was 3.8%.

|  | A | B | C | D |
|---|---|---|---|---|
| 2,5-diamino-4-chloro benzoic acid isobutyl ester (g) | 10.0 | 12.8 | 15.7 | 18.4 | 21.4 |
| Pouring time (minutes) | 5 | 4.5 | 4 | 3.5 | 2 |
| Hardening time (mins.) | 15 | 12 | 10 | 7 | 5 |
| Shore hardness D (DIN 53505) | 40 | 47 | 56 | 66 | 68 |
| Tensile strength (mPa) | 41.0 | 39.0 | 35.5 | 32.0 | 30.0 |
| Tear propagation resistance (KN/m) | 68 | 72 | 75 | 95 | 98 |
| Elasticity (%) | 38 | 38 | 38 | 42 | 42 |

Increasing amounts of 2,5-diamino-4-chlorobenzoic acid isobutyl ester produced a distinct increase in the hardness and tear propagation resistance of these elastomers without significantly affecting their elasticity.

EXAMPLE 13

After degassing at 80° C., 100 parts by weight of the polyisocyanate urea suspension mentioned in Example 4 (NCO-content 5.5%) are stirred with 11.0 parts by weight of 3,5-diethyl-2,4-diaminotoluene. After a pouring time of 2 minutes and a hardening time of 10 minutes, an elastic molding is obtained which, after tempering for 24 hours at 120° C., shows the following mechanical properties:

| | | |
|---|---|---|
| Tensile strength (mPa) | = | 20.4 |
| Elongation at break (%) | = | 380 |
| Tear propagation resistance (KN/m) | = | 33.5 |
| Shore hardness A | = | 84 |
| Elasticity (%) | = | 49 |

EXAMPLE 14

A mixture of 100 parts by weight of the polyisocyanate urea suspension mentioned in Example 7, 12 g of 1,4-butane diol and 0.2 g of stearylamide is stirred at 80° C. with 35.8 g of molten 4,4'-diisocyanatodiphenyl methane, after which the reaction mixture is poured into molds heated to 80° C. After storage for about 2 months at from 200° to 220° C., the thermoplastic polyurethane test specimen is melted and its melt viscosity determined. From the distinct increase in melt viscosity over a period of 30 minutes it is apparent that the complete reaction of the excess 1,4-butane diol with the heterogeneous polyisocyanate urea takes place only now so that i.e., it is only now that the final mechanical properties of the elastomers are obtained.

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:
1. A suspension of
   (a) an isocyanato urea corresponding to the following general formula:

OCH—R—NH—CO—NH—[R—NH—CO—NH]$_m$—R—NCO wherein
   R represents a difunctional aromatic radical obtained by removing the isocyanate groups from an aromatic diisocyanate and
   m represents 0 or an integer of 1 to 5,
   in
   (b) an isocyanate prepolymer corresponding to the following general formula:

D—(O—CO—NH—A—NCO)$_n$ wherein
   A represents a radical obtained by removing the isocyanate groups from an organic diisocyanate,
   D represents a radical obtained by removing the hydroxyl groups from an n-functional polyhydroxyl compound having a molecular weight of from 500 to 8000, and
   n represents an integer from 2 to 4, said suspension being liquid at room temperature or being liquefiable by heating to at most 80° C.
2. Suspension as claimed in claim 1.
3. A process for producing the suspension as claimed in claim 1 comprising:
   (a) mixing
      (1) an aromatic diisocyanate corresponding to the general formula: R(NCO)$_2$ wherein R represents a difunctional aromatic radical obtained by removing the isocyanate groups from an aromatic diisocyanate
      (2) an isocyanate prepolymer corresponding to the general formula: D—(O—CO—NH—A—NCO)$_n$ wherein
         A represents a radical obtained by removing the isocyanate groups from an organic diisocyanate,
         D represents a radical obtained by removing the hydroxyl groups from an n-functional polyhydroxyl compound having a molecular weight of from 500 to 8000, and
         n represents an integer from 2 to 4; and
   (b) reacting the resulting mixture from (1) and (2) with 0.4 to 0.8 mol of water per mol of said aromatic diisocyanate or with a corresponding quantity of a compound splitting off water.

* * * * *